United States Patent [19]
Kaneko et al.

[11] Patent Number: 4,896,677
[45] Date of Patent: Jan. 30, 1990

[54] ELECTROCARDIOGRAPHIC WAVEFORM DISPLAY APPARATUS, AND METHOD OF EXPRESSING ELECTROCARDIOGRAPHIC WAVEFORMS

[75] Inventors: Mutsuo Kaneko; Isamu Suzuki, both of Tokyo; Chuichi Sato, Chofu; Noriko Igarashi; Yumi Nishimura, both of Tokyo, all of Japan

[73] Assignee: Fukuda Denshi Kabushiki Kaisha, Tokyo, Japan

[21] Appl. No.: 285,759

[22] Filed: Dec. 16, 1988

[30] Foreign Application Priority Data

Dec. 26, 1987 [JP] Japan ............................ 62-330933
Jul. 25, 1988 [JP] Japan ............................ 63-183585

[51] Int. Cl.⁴ .......................................... A61B 5/04
[52] U.S. Cl. .................................. 128/696; 128/710
[58] Field of Search ............... 128/710, 711, 712, 696

[56] References Cited

U.S. PATENT DOCUMENTS

| | | | |
|---|---|---|---|
| 3,215,136 | 11/1965 | Holter et al. ........... | 128/711 |
| 3,267,933 | 8/1966 | Mills et al. ............. | 128/711 |
| 3,874,370 | 4/1975 | Harris et al. ........... | 128/711 |
| 3,960,140 | 6/1976 | Buxton ................... | 128/712 |
| 4,006,737 | 2/1977 | Cherry ................... | 128/710 |
| 4,098,267 | 7/1978 | Stein et al. ............ | 128/711 |
| 4,513,294 | 4/1985 | Anderson et al. ..... | 128/710 |

*Primary Examiner*—Lee S. Cohen
*Assistant Examiner*—Scott Getzow
*Attorney, Agent, or Firm*—Lynn L. Augspurger

[57] ABSTRACT

An electrocardiographic waveform recorder, analyzer, printer and display for superimposing in synchronization, for a predetermined period of time, ECG waveforms. The waveforms are superimposed and synchronized with a predetermined characteristic ECG point (the R-wave peak point) and a plural number of waveforms are expressed while the superimposed positions, at which they are expressed, is changed at fixed intervals of the waveforms, permitting state of deviation recognition.

In addition, an ST trend graph and a heart rate output are used for comparisons with environmental conditions. Also, data is recorded continuously over time and displayed and printed at intervals corresponding to the occurrence of the characteristic point of the waveform which permits change in the superimposed waveform display positions. A P wave, a T wave and a QRS wave can be extracted, along with their crest values and the crest value at an arbitrary position in an ST region. A T-wave peak may serve as a characteristic time point value. Outputs can be the P-wave trend graph and the P wave, along with the trend graph of the QRS-wave peak and the QRS wave and a trend graph of the T-wave peak and the T wave all possibly displayed on the same time axis, in the same time interval display region.

18 Claims, 11 Drawing Sheets

ELECTROCARDIOGRAPHIC WAVEFORM DISPLAY APPARATUS, AND METHOD OF EXPRESSING ELECTROCARDIOGRAPHIC WAVEFORMS

BACKGROUND OF THE INVENTION

This invention relates to an electrocardiographic waveform display apparatus and a method of expressing electrocardiographic waveforms in which a plurality of electrocardiographic waveforms are expressed in a time series.

As an example of the prior art, an apparatus as disclosed in the specification of Japanese Patent Application Laid-Open No. 57-81329 is designed to record electrocardiographic waveforms continuously over an extended period of time and subsequently reproduce the recorded waveforms so that any changes therein can be distinguished, thereby making it possible to discover heart ailments and to accurately identify the status thereof. Some of these conventional apparatus are designed to record for a period of 24 hours or longer.

Apparatus for the purpose of reading and visually displaying the recorded waveforms mainly employ any of the following three methods to display the recorded waveforms:

(1) a method in which recorded waveforms are compressed and then continuously recorded or displayed;

(2) a method which places emphasis on the fact that an ST waveform contained in the electrocardiographic waveforms is of great importance in judging the presence of heart disease, and which displays the ST waveform on a CRT screen by a superimposing technique using R-wave synchronization; and (3) a method of providing a trend display at any measurement point.

However, method (1) is disadvantageous in that the recorded waveforms are small and it is difficult to accurately recognize the ST portion. Method (2) makes it possible to recognize changes over several beats only and the method does not lend itself to recording on paper or the like. With method (3), only a change in the ST portion at specific point can be determined, thus making it impossible to accurately judge an entire waveform.

SUMMARY OF THE INVENTION

An object of the present invention is to solve the foregoing problems.

According to the present invention, the foregoing object is attained by providing an electrocardiographic waveform display apparatus comprising detecting means for detecting a predetermined characteristic point contained in an inputted electrocardiographic waveform, waveform superimposing means for superimposing a predetermined amount of an electrocardiographic waveform in synchronization with the detected characteristic point, and output means for displaying and outputting a plurality of electrocardiographic waveforms, which are superimposed by the waveform superimposing means, while changing display positions.

In the above arrangement, an electrocardiographic waveform is superimposed in synchronization with a predetermined characteristic point in the waveform, and a number of the superimposed waveforms are expressed while changing, at fixed amounts, positions at which the superimposed waveforms are expressed. This makes it possible to easily recognize the state of any deviation in an electrocardiographic waveform.

Further, there is provided an electrocardiographic waveform display apparatus comprising detecting means for detecting a predetermined characteristic point contained in an inputted electrocardiographic waveform, waveform superimposing means for superimposing a predetermined amount of an electrocardiographic waveform in synchronization with the detected characteristic point, superimposed waveform output means for displaying and outputting a plurality of electrocardiographic waveforms, which are superimposed by the waveform superimposing means, while changing display positions, sampling means for sampling a predetermined partial waveform every predetermined amount of an inputted electrocardiographic waveform, and partial waveform output means for displaying and outputting a plurality of sampled waveforms while changing display positions.

In the above arrangement, an electrocardiographic waveform is superimposed in synchronization with a predetermined characteristic point in the waveform, a number of the superimposed waveforms are expressed while changing the display position at a fixed amount, and at least one specific partial waveform contained in the superimposed electrocardiographic waveforms is displayed in plural form in correspondence with the superimposed waveform display region. This makes it possible to display the state of a deviation in an electrocardiographic waveform.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Embodiments of the present invention will now be described in detail with reference to the drawings.

<First Embodiment>

Figure 1:
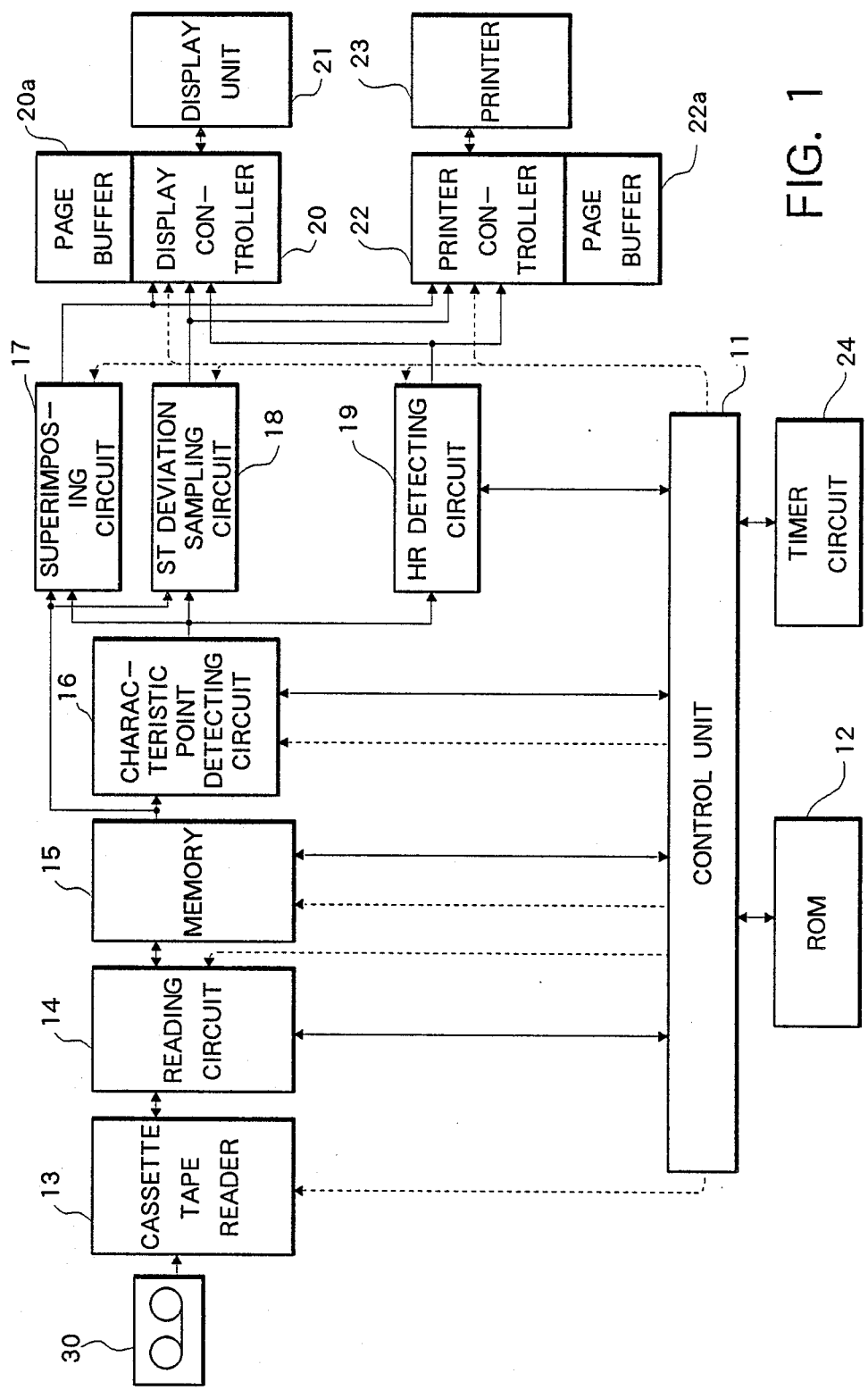
FIG. 1 is a block diagram illustrating an electrocardiogram analyzing apparatus in an embodiment according to the present invention.

FIG. 1 is a block diagram illustrating an electrocardiogram analyzing apparatus in an embodiment according to the present invention. The apparatus includes a control unit 11 which performs overall control of the embodiment in accordance with a program, an example of which is as shown in FIG. 4, stored in a ROM 12. The latter also stores various parameters in addition to the program. A cassette tape reader 13 reads electrocardiographic waveforms from a cassette tape 30 on which the electrocardiographic waveforms are recorded by a recording apparatus of the kind shown in FIG. 2 by way of example. The cassette tape reader 13 is connected to a reading circuit 14 which controls the tape reader 13 to read electrocardiographic waveforms from the tape 30, digitize the waveforms and deliver the binary output to a memory 15, which is capable of preserving at least two beats of an electrocardiographic waveform from the reading circuit 14.

A characteristic point detecting circuit 16 reads out an electrocardiographic waveform stored in the memory 15 and detects a characteristic point, such as an R-wave peak point, designated by the control unit 11. A superimposing circuit 17 superimposes the electrocardiographic waveform from memory 15 in synchronization with the characteristic point detected by the circuit 16. The superimposing circuit 17 performs electrocardiographic waveform superimposing processing until a display position change command arrives from the control unit 11; meanwhile, the electrocardiographic waveform read from the memory 15 is superimposed in its entirety in a form synchronized to the characteristic point. Numeral 18 denotes an ST deviation sampling circuit for sampling a value of the read electrocardiographic waveform at an arbitrary timing (an arbitrary timing from an S point) decided between S-T. A heart rate (HR) detecting circuit 19 detects heart rate by measuring the time interval at which, e.g., the R-wave peak of an electrocardiographic waveform is generated. A display controller 20 gathers the superimposed waveform of the electrocardiographic waveform from the superimposing circuit 17, an ST trend graph from the ST deviation sampling circuit 18, and HR trend graph data from the HR detecting circuit 19, and displays the results on a CRT screen. The display controller 20 is connected to a display unit 21 for displaying predetermined data on the CRT screen. Numeral 22 denotes a printer controller which gathers the ST trend graph from the ST deviation sampling circuit 18 and each item of data in the HR trend graph data from the HR detecting circuit 19, and which prints out the results on a printer 23. A timer circuit 24 is connected to the control unit 11.

Figure 2:
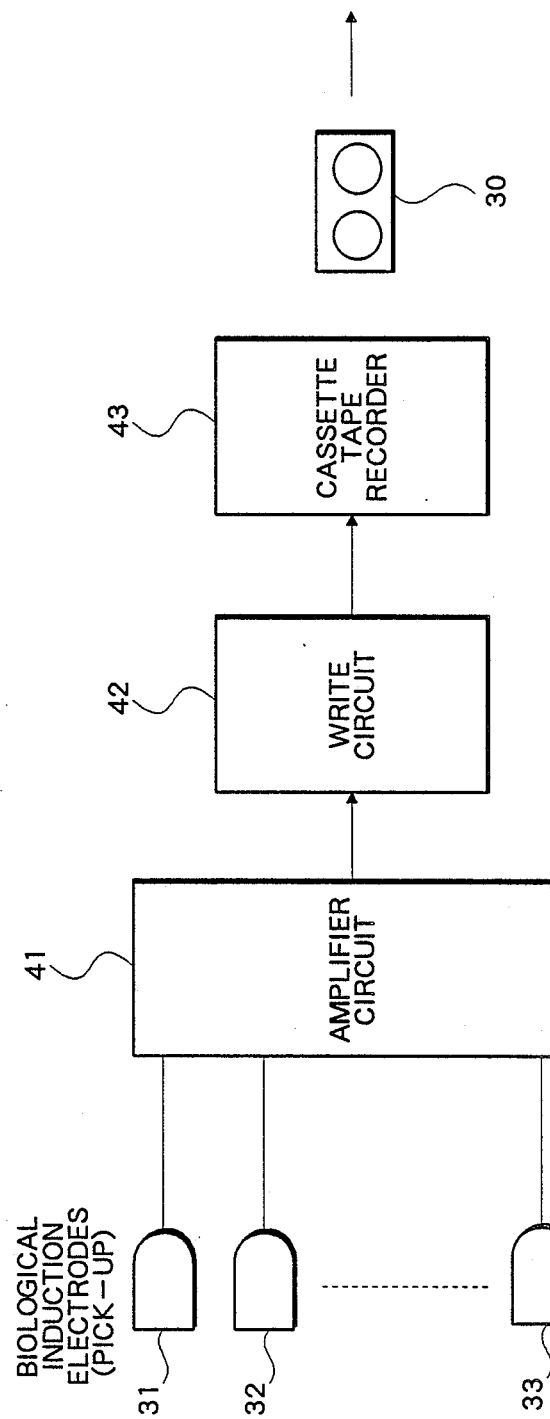
FIG. 2 is a block diagram of an electrocardiographic waveform recording apparatus used in the present embodiment to record an electrocardiographic waveform.

FIG. 2 is a block diagram of an electrocardiographic waveform recording apparatus for recording electrocardiographic waveforms from a patient on the cassette tape 30. The apparatus includes biological induction electrodes 31, 32, 33 affixed to the surface of a living body to acquire an electrocardiographic waveform, an amplifier circuit 41 for amplifying the electrocardiographic waveform from the electrodes 31-33, and a write circuit 42 for recording the electrocardiographic waveform on a cassette tape recorder 43. The latter is for recording data from the write circuit 42 on the cassette tape 30.

Figure 3:
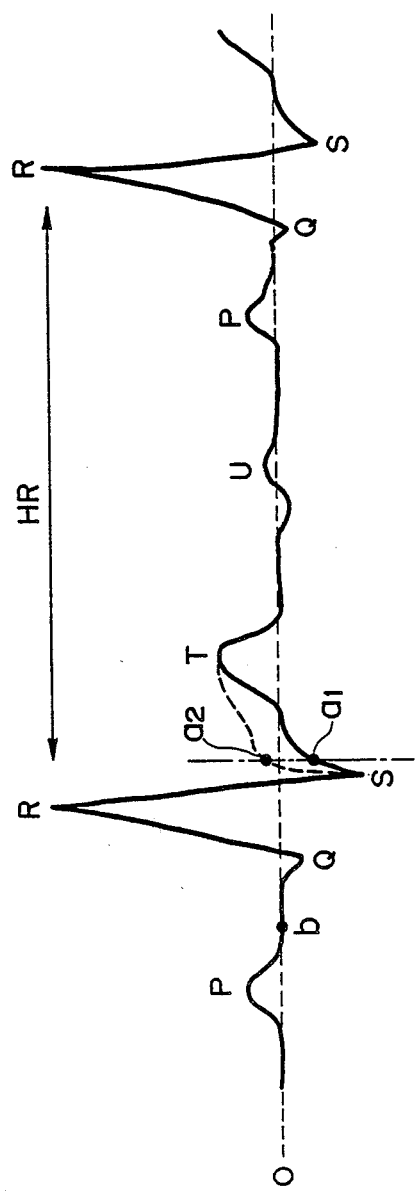
FIG. 3 is a view for describing an electrocardiographic waveform.

The electrocardiographic waveform introduced by the electrodes 31-33 ordinarily is a repeating spike-shaped wave of the kind shown in FIG. 3 and is composed of successive P, Q, R, S and T waves. The P wave is caused by atrial excitation, and the QRS group by ventricular excitation. The T wave is caused by vetricular recovery. The T wave is sometimes followed by a small rise referred to as a U wave. The characteristic point detecting circuit 16 reads out the electrocardiographic waveform data from the memory 15 in a time series and detects peak points or bottom points. The detected peak points or bottom points are compared in terms of their generation time intervals and prevailing levels in order to determine which spike has been detected in the electrocardiographic waveform from the correlation among the detected peak points and bottom points.

For example, the first detected peak point is regarded as the P-wave peak point, which serves as a reference point for characteristic point detection, monitoring is performed to determine if a bottom point corresponding to the Q-wave peak point has been detected within a predetermined time period, and monitoring is performed to determine whether a peak point, which corresponds to an R-wave peak point having a level difference larger than one predetermined, has been detected within a predetermined time period following detection of the bottom point corresponding to the Q-wave peak point. This process is repeated in similar fashion to detect the S-wave peak point, the T-wave peak point, etc.

Characteristic point detection processing of the present embodiment is not limited to the above-described method. It is permissible to adopt an arrangement in which a peak point having a level corresponding to the R-peak point, which is the most easily detected peak point in the electrocardiographic waveform, is detected first, a search is performed to successively detect bottom and peak points within predetermined time periods, thereby successively detecting the R, Q and P waves in the order mentioned, after which the S and P waves are detected in the order mentioned.

If a prescribed peak wave is not detected by thus detecting the peak points of the spike-shaped waves, this is taken as meaning that the electrocardiographic waveform characteristic point detection did not start from the correct reference point, then the next peak point is taken as a new reference point and the next characteristic point detection processing is executed. Sampling points for trend graph preparation can also be detected using the abovementioned characteristic point detection positions as a reference.

Arrhythmia and impediments to excitation transfer can be judged from the time relationships of the spike-shaped waves thus detected.

Ischemic heart disease, myocarditis and pericarditis of a myocardial infarct or the like, hypertrophy of the left and right auricles and ventricles, electrolytic abnormalities, medicinal action and abnormal internal secretions can be diagnosed from changes in the shapes of the spike waves.

In order to carry out these diagnoses, easy recognition of the state of a change in waveform is essential. Since the locations at which changes occur are substantially decided by the region undergoing diagnosis, the characteristic point detecting circuit 16 should be instructed to detect a characteristic point immediately in front of the region in such a manner that it is easy to recognize a change in the region where the spike wave changes.

A deviation in the ST region is most often used in these diagnoses.

First of all, therefore, a crest value at any measurement point is measured for ST trend graph preparation similar to that of the prior art by means of the ST deviation sampling circuit 18. The ST deviation sampling circuit 18 is synchronized taking, e.g., the R-wave crest as a measurement point, and crest value is sampled. The crest value is the potential difference, from a reference point b on a reference level, of a specific point on a specific line, indicated by the one-dot chain line in FIG. 3, following elapse of a predetermined time period from the R wave. The specific point can be the point $a_1$ indicated by the solid line or the point $a_2$ indicated by the dashed line.

The crest value is negative in the case of point $a_1$ and positive in the case of $a_2$. An ST trend graph is obtained by successively displaying these crest values as a trend graph.

In this embodiment, in addition to the ST trend graph, a predetermined amount of an electrocardiographic waveform is superimposed and outputted by the superimposing circuit 17 taking the R-wave peak, which is a characteristic point immediately in front of, e.g., the ST segment, as a synchronizing point. In this way an ST deviation can be recognized at a single glance.

Figure 5:
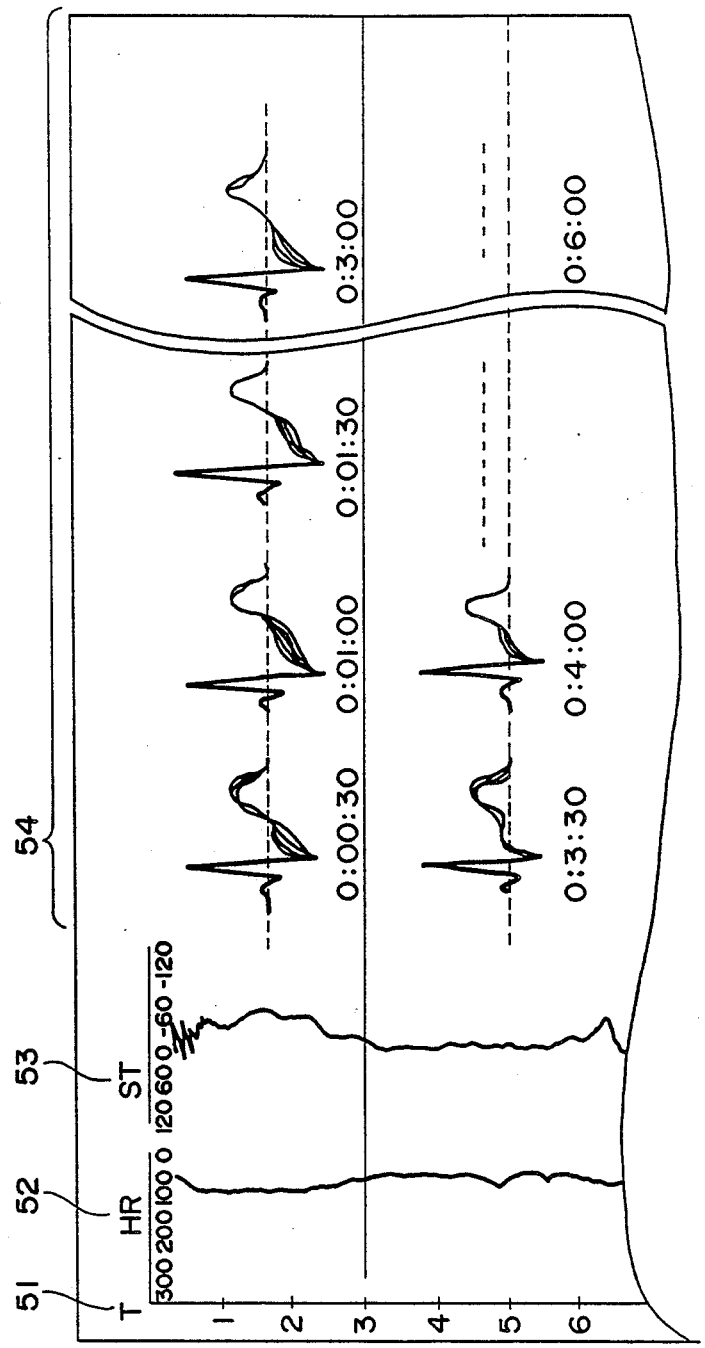
FIG. 5 is a view illustrating an example of an electrocardiographic waveform output according to the present embodiment.

Specifically, in accordance with the present embodiment, the R-wave peak point is adopted as a characteristic point, as shown in FIG. 5 which will be described below, a predetermined amount (e.g., a 30-second interval) of the electrocardiographic waveform is superimposed in synchronization with this characteristic point, and the result is displayed/outputted while successively changing the display position. In this way the size of the waveform can be increased in comparison with a compressed electrocardiogram, and the ST deviation can be recognized at a glance.

Furthermore, the HR graph and the ST trend graph recording the crest values of arbitrary positions of the ST region are gathered and simultaneously displayed/outputted at the same time as the superimposed waveforms, thereby making it possible to easily recognize a number of electrocardiographic waveform deviations.

Figure 4A:
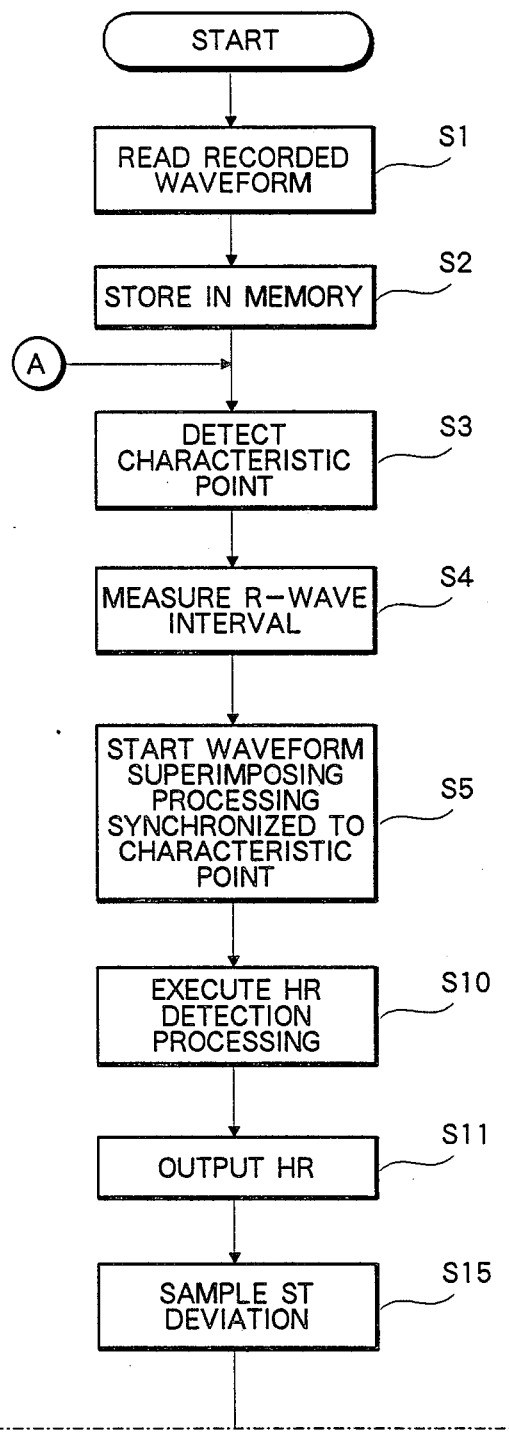
FIGS. 4A and 4B show electrocardiographic waveform output control flowchart in the present embodiment.
Figure 4B:
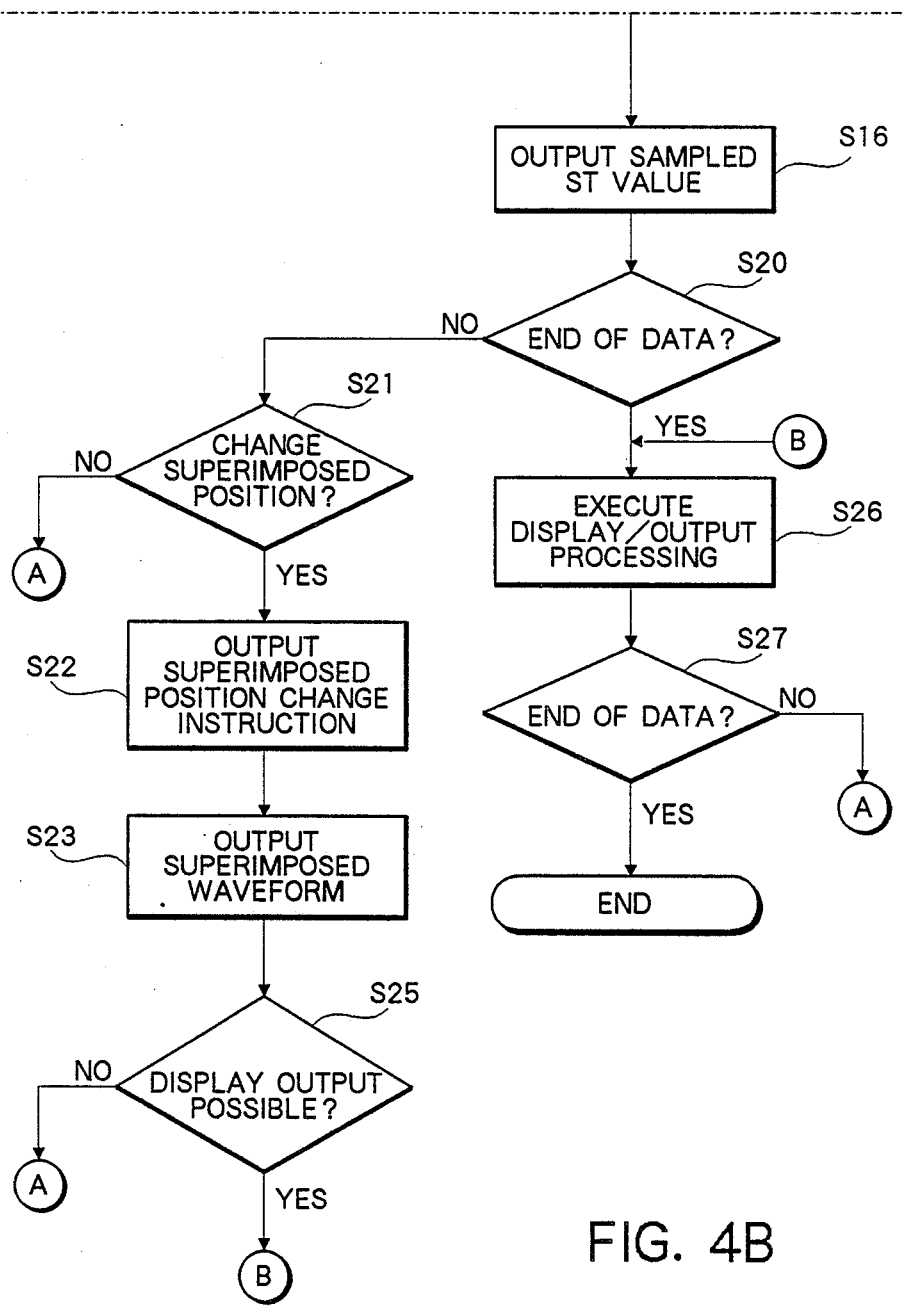

Control of the electrocardiographic output of the apparatus embodied in FIG. 1 will now be described in detail with reference to the flowcharts of FIGS. 4A and 4B.

When the cassette tape 30 having the recorded electrocardiographic waveform is inserted into the cassette tape reader 13 of the present apparatus and the apparatus is started, the program proceeds to a step S1. Here the control unit 11 instructs the reading circuit 14 to control the cassette tape reader 13 so that the recorded electrocardiographic waveform is read out in successive fashion. At this time the read time information is set in the timer circuit 24, which is made to keep track of time at the time of recording. The waveform is written in the memory 15 at a step S2. The capacity of the memory 15 should be sufficient for more than two beats of the electrocardiographic waveform. The steps S1, S2 are subsequently executed continuously. Next, at a step S3, the electrocardiographic waveform written in the memory 15 is simultaneously delivered to the characteristic point detecting circuit 16, where the designated characteristic point, namely the R-wave peak point, is detected. Time from the R-wave peak point one beat earlier is measured at a step S4. This is performed by writing in the timekeeping data from the timer circuit 24.

Next, at a step S5, the superimposing circuit 17, in synchronization with the detection timing of this characteristic point, superimposes the detected electrocardiographic waveform of the corresponding characteristic point at a timing which is the same as that of the previously superimposed waveform. Accordingly, the R-wave peak points of the superimposed electrocardiographic waveforms all have the same position.

This is followed by a step S10, at which the HR detecting circuit 19 computes heart rate from the detected time interval of characteristic point (R-wave peak), which time interval was measured at the step S4. The heart rate obtained is outputted to the display controller 20 and printer controller 22 at the same time as the time information at a step S11. The display controller 20 and printer controller 22 develop the HR value on a time axis corresponding to the display output position of page buffers 20a, 22a which store a predetermined amount of the output information containing the HR value.

Next, at a step S15, the ST deviation sampling circuit 18 is started to obtain an ST peak value (the peak value from the reference level) of a position prevailing upon elapse of a predetermined time from the characteristic point, as mentioned above, and this peak value is sampled as the ST deviation value at this position. The next step S16 calls for this sampled ST value to be outputted to the display controller 20 and printer controller 22 at the same time as the time information. The display controller 20 and printer controller 22 develop this sampled value of ST deviation on a time axis corresponding to the ST deviation display output position of page buffers 20a, 22a. For example, in the present embodiment, this ST deviation and HR are expressed on the same time axis, as shown at numerals 52 and 53 in FIG. 5, and the locations thereof have different display positions. The time axis is a vertical axis of identical times.

Next, it is determined at a step S20 whether the recorded information from the cassette tape 30 has stopped arriving. If there is no more recorded information, the program proceeds to a step S26. If there is still recorded information, the program proceeds to a step S21, where it is determined whether a predetermined amount (a predetermined time interval) of the electrocardiographic waveform has been superimposed. If a predetermined amount (e.g., 30 seconds) has not been superimposed, then the program returns to the step S3 where characteristic point detection processing for the next electrocardiographic waveform is executed.

When processing for superimposing the predetermined amount of the electrocardiographic waveform has been executed, the program proceeds from the step S21 to a step S22, at which a command for altering the superimposed waveform display position is outputted to the superimposing circuit 17, display controller 20 and printer controller 22, whereby the superimposed waveform being held is reset. The display controller 20 and printer controller 22 that have received this command develop this superimposed waveform in the page buffers at a position corresponding to the display position. Next, at a step S25, it is determined whether the data developed in the page buffers by the controllers 20, 22 can be outputted, namely whether it is possible to output one line (or one page). If it is as yet impossible to output the data, the program returns to the step S3 to execute overlapping processing for the next electrocardiographic waveform.

If it is determined at the step S25 that output of the display is possible, the program proceeds to a step S26, at which one line (one row) of data is displayed on the display unit 21 under the control of the display controller 20 and one line of data is printed out on the printer 23 under the control of the printer controller 22. In this display/output operation, the superimposed waveform developed in the page buffers is outputted while changing the display position at predetermined times, and the HR trend graph and ST trend graph are outputted simultaneously, with the time corresponding to the superimposed waveform display interval of one row serving as the vertical time axis.

When data display and print-out end, the program proceeds to a step S27, at which it is determined whether this is the end of the recorded information. If it is not the end of recorded information, then the program returns to the step S3 to execute processing for the next electrocardiographic waveform. If this is the end of recorded information, on the other hand, then processing is terminated.

In accordance with the embodiment described above, the detected R wave is written in superimposed form in synchronization with the R peak point, and the position at which the R wave is written is shifted at a fixed time interval. This waveform is outputted upon being combined with the ST trend graph and HR trend graph obtained according to the conventional method, thereby making it possible to easily recognize the extent of ST change and the change in the shape thereof.

Superposition makes it possible to express an entire beat in a small recording area and on a display screen.

An example of an output thus obtained is shown in FIG. 5.

In FIG. 5, numeral 51 denotes a time axis T, in which one graduation corresponds to one minute. Numeral 52 denotes the HR trend graph indicating the change in HR value at every moment in accordance with the time axis T. Numeral 53 denotes the ST trend graph indicating the change in ST peak value at every moment in accordance with the time axis T. Numeral 54 denotes the electrocardiographic waveform display in which the electrocardiographic waveform is superimposed every 30 seconds and a display is made in one row while changing the display position. In this embodiment, one row corresponds to three minutes.

<Second Embodiment>

It is described above that the peak point of the R wave is detected as a characteristic point, the electrocardiographic waveform is superimposed in synchronization with this peak point, and HR, ST are displayed as biological information along with the waveform. However, the characteristic point and other displayed biological information are not limited to those in the above-described embodiment. Any kind of biological information recorded on the cassette tape will suffice. It is also permissible to the biological information to be recorded on a recording medium other than the cassette tape.

Furthermore, the display and output method is not limited to that described above.

Figure 6:
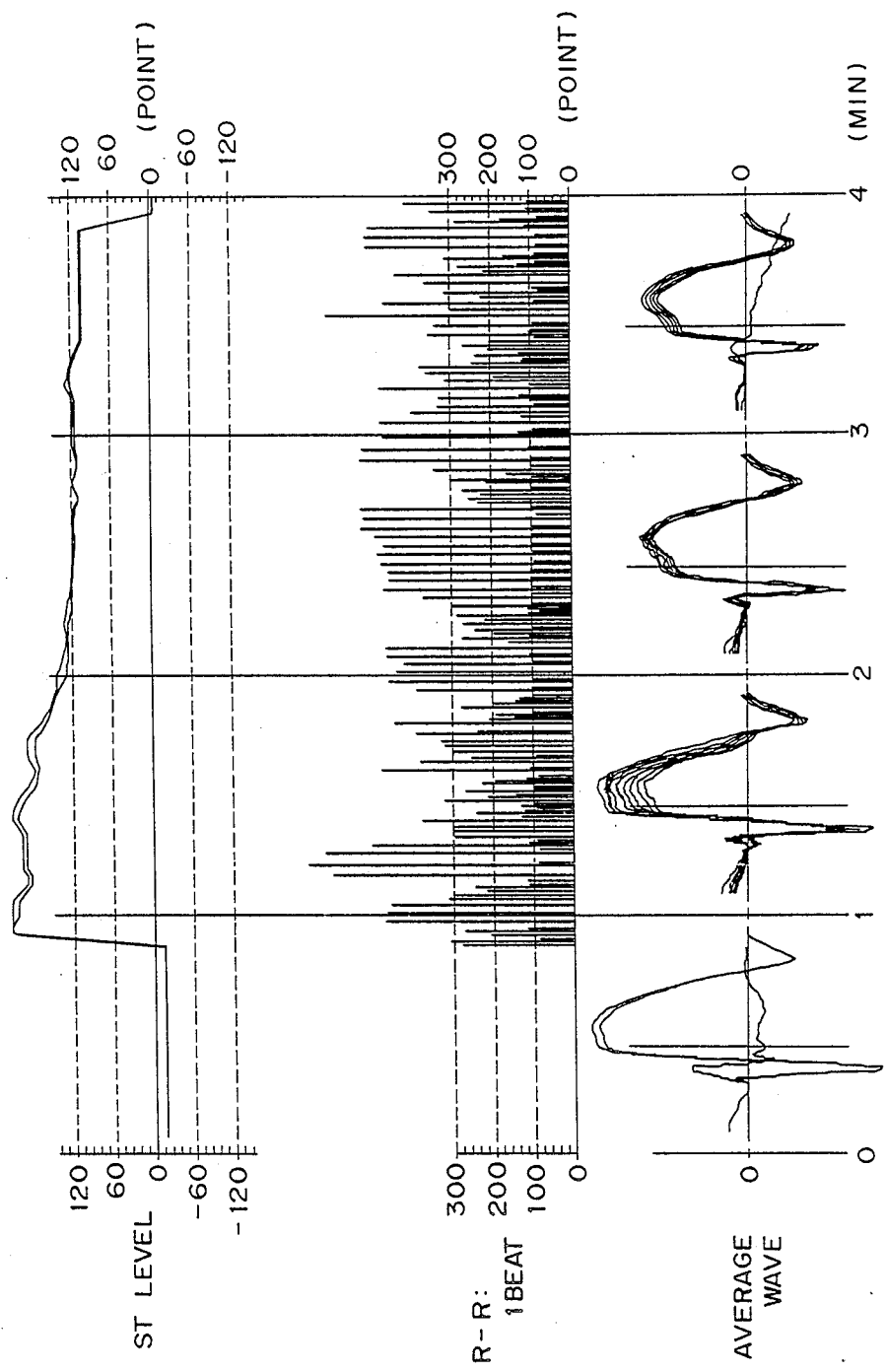
FIG. 6 is a view showing an example of an electrocardiographic waveform output in a second embodiment of the present invention.

FIG. 6 illustrates an example of display/output by another method in synchronization with the same characteristic point of the first embodiment.

In FIG. 6, rather than displaying the ST trend graph and the like on a time axis perpendicular to the electrocardiographic waveform, as described above, these are displayed on the same axis. Also, the characteristic point can be taken as the point P shown in FIG. 3.

In accordance with the present embodiment as described above, a predetermined amount of the electrocardiographic waveform is superimposed in synchronization with, e.g., the P wave or R wave of the electrocardiographic waveform, and this is displayed while successively changing the display position. Accordingly, the waveforms can be displayed in larger size in comparison with the case in which the entire waveforms are displayed upon being compressed within limits decided by an identical time axis. Consequently, the shape of the electrocardiographic waveform can be easily ascertained even down to very fine portions.

In addition, since a large number of waveforms are superimposed, deviations between waveforms can be recognized very easily. Also, along with the superimposed waveforms, the ST trend waveform, for example, can be shown using the same time axis or orthogonal time axes and the position of the superimposed waveforms in time corresponding to the ST trend waveform is displayed so as to be recognizable. As a result, the extent of ST change can be recognized at a glance and a change in waveform can be checked by specifying the corresponding superimposed waveform upon observing this waveform. This makes it possible to identify a change in a number of electrocardiographic waveforms very quickly and reliably.

Consequently, when 24 hours of an electrocardiographic waveform is printed out or displayed, the degree of change therein can be ascertained reliably in a short period of time, and observing the change enables an appropriate diagnosis to be made.

In accordance with the invention as described above, a change in an electrocardiographic waveform can be easily recognized and a number of electrocardiographic waveforms can be scrutinized quickly and accurately as shown in FIG. 6, as an alternative embodiment to the showing of FIG. 5, both illustrating, as examples, subsequent electrocardiographic waveforms which are superimposed on each other after a certain time interval has elapsed.

<Third Embodiment>

In the embodiments described above, a number of electrocardiographic waveforms are superimposed and displayed in synchronization with a predetermined characteristic point. However, the invention is not limited to the foregoing. A plurality of specific partial waveforms contained in a superimposed electrocardiographic waveform can be displayed and a change in the specific partial waveform with time can be ascertained. Such an arrangement is also covered by the scope of the invention.

Figure 7:
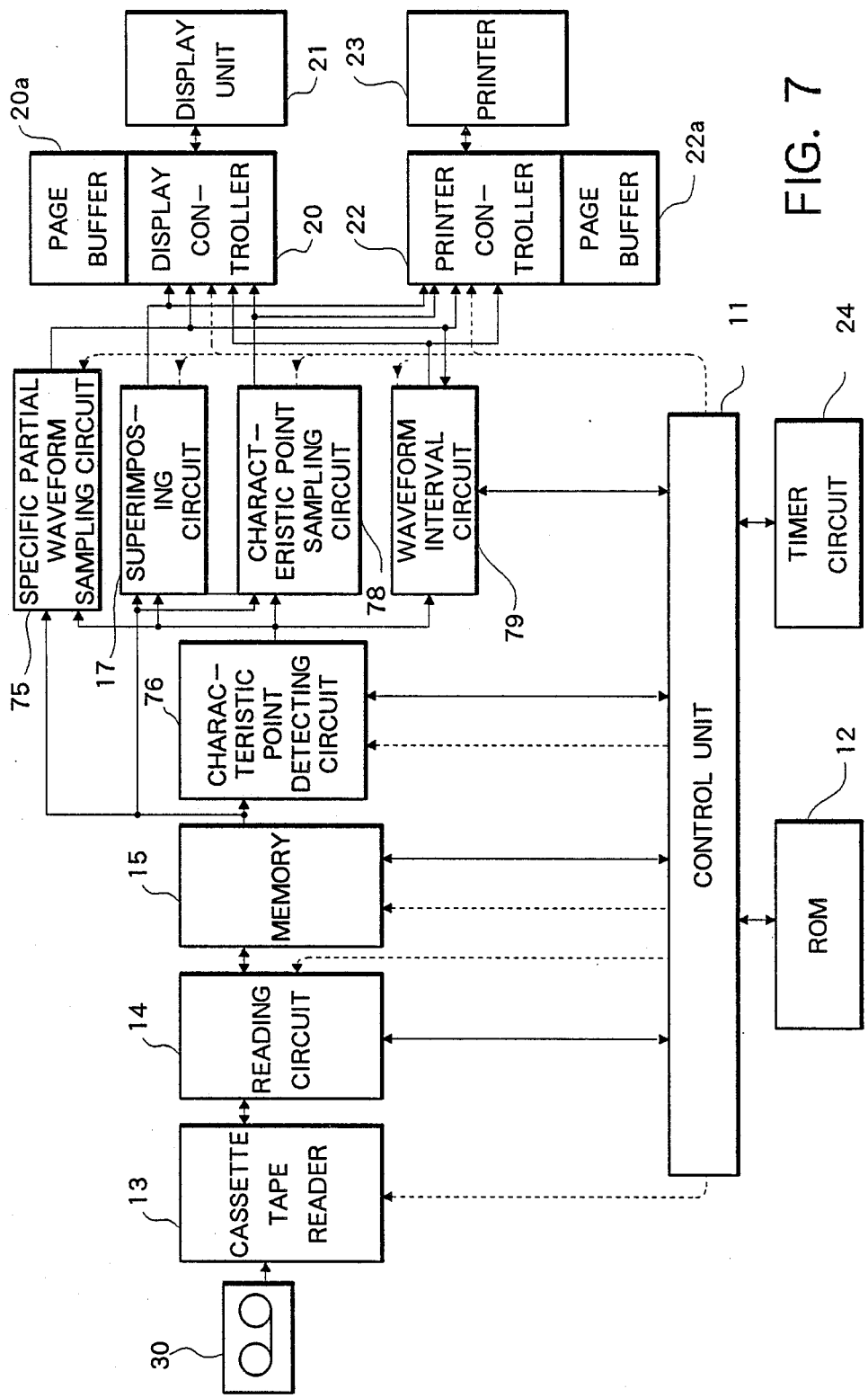
FIG. 7 is a block diagram illustrating an electrocardiogram analyzing apparatus in a third embodiment according to the present invention.

FIG. 7 is a block diagram of an electrocardiogram analyzing apparatus in a third embodiment of the present invention adapted to perform the above-described operation.

Portions in FIGS. 7 identical with those shown in FIG. 1 are designated by like reference characters.

The apparatus includes the control unit 11 which performs overall control of the embodiment in accordance with a program, an example of which is as shown in Fig. 8, stored in the ROM 12. The latter also stores various parameters in addition to the program. The cassette tape reader 13 reads electrocardiographic waveforms from the cassette tape 30 on which the electrocardiographic waveforms are recorded by a recording apparatus. The cassette tape reader 13 is connected to the reading circuit 14 which controls the tape reader 13 to read electrocardiographic waveforms from the tape 30, digitize the waveforms and deliver the binary output to the memory 15, which is capable of preserving at least two beats of an electrocardiographic waveform from the reading circuit 14. The superimposing circuit 17 superimposes the electrocardiographic waveform from memory 15 in synchronization with a characteristic point detected by a characteristic point detecting circuit 76. The superimposing circuit 17 performs electrocardiographic waveform superimposing processing until a display position change command arrives from the control unit 11; meanwhile, the electrocardiographic waveform read from the memory 15 is superimposed in its entirety in a form synchronized to the characteristic point.

The display controller 20 gathers and develops the superimposed waveform of the electrocardiographic waveform from the superimposing circuit 17, a trend graph of each characteristic point from a characteristic point sampling circuit 78, waveform interval data from a waveform interval detecting circuit 79, and a sampled partial waveform from a specific partial waveform sampling circuit 75, and displays the results on a CRT screen of the display unit 21. The display unit 21 is for displaying predetermined data on the CRT screen. The printer controller 22 gathers and develops, in the internal page buffer 22a, the superimposed electrocardiographic waveform from the superimposing circuit 17, the trend graph of each characteristic point from the characteristic point sampling circuit 78, the waveform interval data from the waveform interval detecting circuit 79, and the sampled partial waveform from the specific partial waveform sampling circuit 75, and prints out the results on the printer 23. The timer circuit 24 is connected to the control unit 11.

The specific partial waveform sampling circuit 75 samples specific partial waveforms, e.g, P, QRS and T waveforms, of an electrocardiographic waveform read from the memory 15 and outputs these waveforms to the display controller 20 and printer controller 22. With a detected corresponding partial waveform peak point, from the characteristic point detecting circuit 76, contained in the electrocardiographic waveform from the memory 15 serving as a reference point, the circuit 75 samples the electrocardiographic waveform within a predetermined range on either side of the reference point and outputs this as a desired partial waveform. Accordingly, the circuit 75 has an internal buffer for storing the partial waveform.

The characteristic point detecting circuit 76 reads the electrocardiographic waveform from the memory 15 and detects a characteristic point, e.g., the R-wave peak point, designated by the control unit 11. The circuit 76 measures the peak value of each characteristic point in the electrocardiographic waveform as well as time up to appearance of the characteristic point, and detects a desired characteristic point upon referring to a relative change or the like between characteristic points. Characteristic point detection processing is as described earlier and need not be discussed in detail again. The characteristic point sampling circuit 78 samples values at arbitrary characteristic points of the electrocardiographic waveform read from the memory 15 and forms a trend graph of a pertinent point. In the present embodiment, the circuit 78 samples the crest value of the P-wave peak, the crest value of the QRS-wave peak, the crest value at any measurement point of the ST region, and the crest value of the T-wave peak. The waveform interval detecting circuit 79 measures the time interval of, e.g., the R-wave peak of the electrocardiographic waveform and detects the electrocardiographic waveform interval.

Ischemic heart disease, myocarditis and pericarditis of a myocardial infarct or the like, hypertrophy of the left and right auricles and ventricles, electrolytic abnormalities, medicinal action and abnormal internal secretions can be diagnosed from changes in the shapes of the spike waves of the electrocardiographic waveform introduced from the biological induction electrodes. In order to carry out these diagnoses, easy recognition of the state of a change in waveform is essential. Since the locations at which changes occur are substantially decided by the region undergoing diagnosis, the characteristic point detecting circuit 76 should be instructed to detect a characteristic point immediately in front of the region in such a manner that it is easy to recognize a change in the region where the spike wave changes.

First of all, therefore, a crest value at a predetermined measurement point is measured for characteristic point trend graph preparation by means of the characteristic point sampling circuit 78. The characteristic point sampling circuit 78 samples the crest values of the P-wave peak, R-wave peak and T-wave peak. Owing to the fact a deviation in the ST region is most often used in diagnosis employing an electrocardiographic waveform, the circuit is synchronized to the R-wave peak as a measurement point, and crest value is ST-sampled. The crest value is at a specific point on a specific line indicated by the one-dot chain line in FIG. 3, following elapse of a predetermined time period from the R wave. The ST sampling point can be the point $a_1$ indicated by the solid line or the point $a_2$ indicated by the dashed line.

The crest value is negative in the case of point $a_1$ and positive in the case of $a_2$. These sampling crest values are successively displayed as a trend graph, and the state of a change in a crest value can be ascertained at a glance.

In this embodiment, in addition to the trend graph of sampled crest values, a partial waveform, which is sampled by the specific partial waveform sampling circuit 75 at predetermined beats of the electrocardiographic waveform read from the cassette tape 30, is outputted upon being superimposed on the trend graph, so that a deviation in the waveform and not just in the crest value of the sampling point can be ascertained at a glance.

More specifically, the P-wave peak crest value trend graph and the P wave are outputted on the same time axis of the same display region, the QRS-wave peak crest value trend graph and the QRS wave are outputted on the same time axis of the same display region, and the T-wave peak crest value trend graph and the T wave are outputted on the same time axis of the same display region.

Further, in the present embodiment, a predetermined amount of an electrocardiographic waveform is superimposed and outputted by the superimposing circuit 17 taking the R-wave peak, which is a characteristic point immediately in front of, e.g., the ST segment, as a synchronizing point. In this way an ST deviation can be recognized at a glance.

Figure 9:
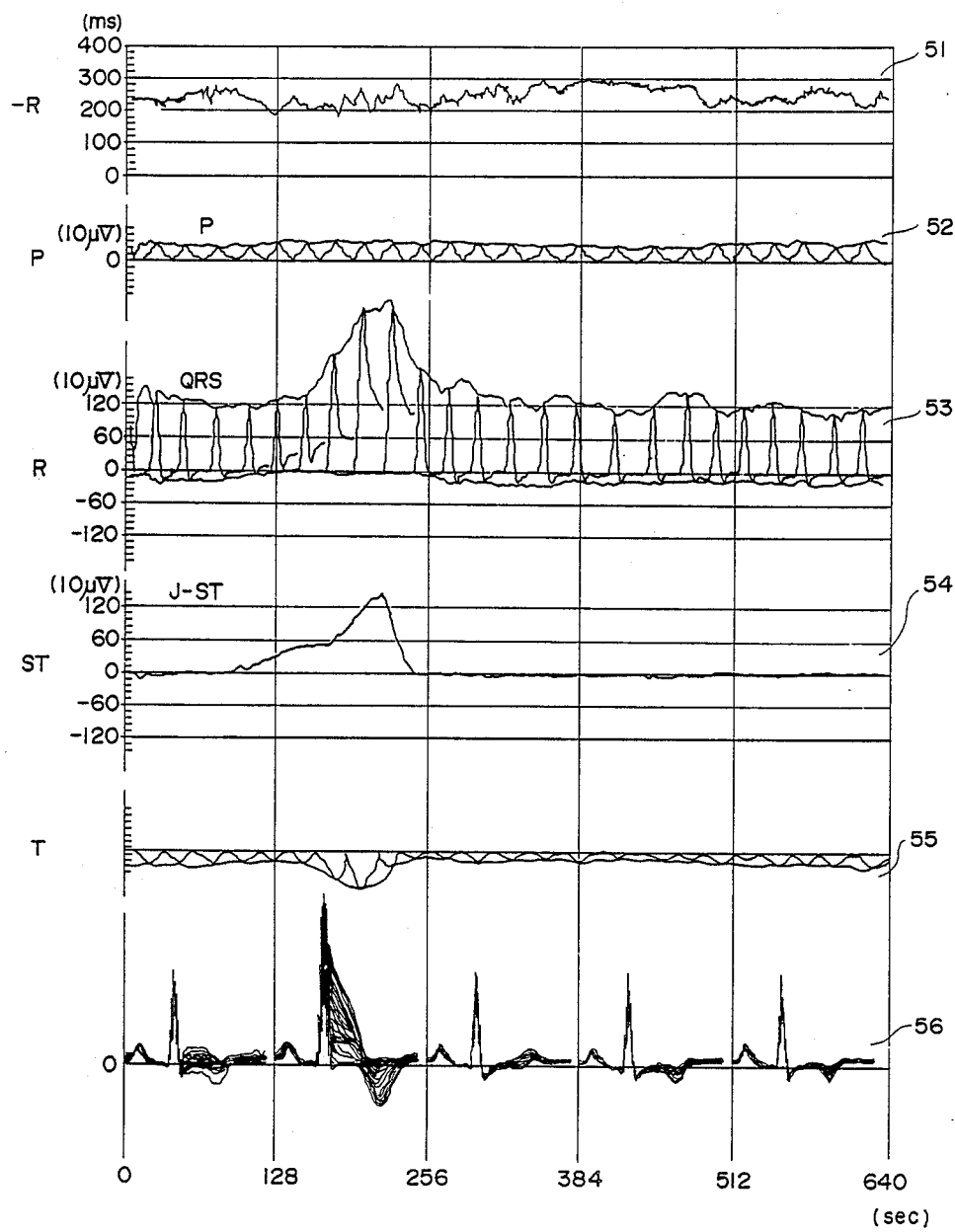
FIG. 9 is a view illustrating an example of an electrocardiographic waveform output according to the third embodiment.

Specifically, in accordance with the present embodiment, the R-wave peak point is adopted as a characteristic point, as shown in FIG. 9 which will be described below, a predetermined amount (e.g., a 128-second interval) of the electrocardiographic waveform is superimposed in synchronization with this characteristic point, and the result is displayed/outputted while successively changing the display position. In this way the size of the waveform can be increased in comparison with a compressed electrocardiogram output, and the ST deviation and the deviation in each of the other waveform portions can be recognized at a glance.

Furthermore, each trend graph and the partial waveforms are gathered and simultaneously displayed/outputted at the same time as the superimposed waveform, thereby making it possible to easily recognize in detail a number of electrocardiographic waveform deviations.

Figure 8A:
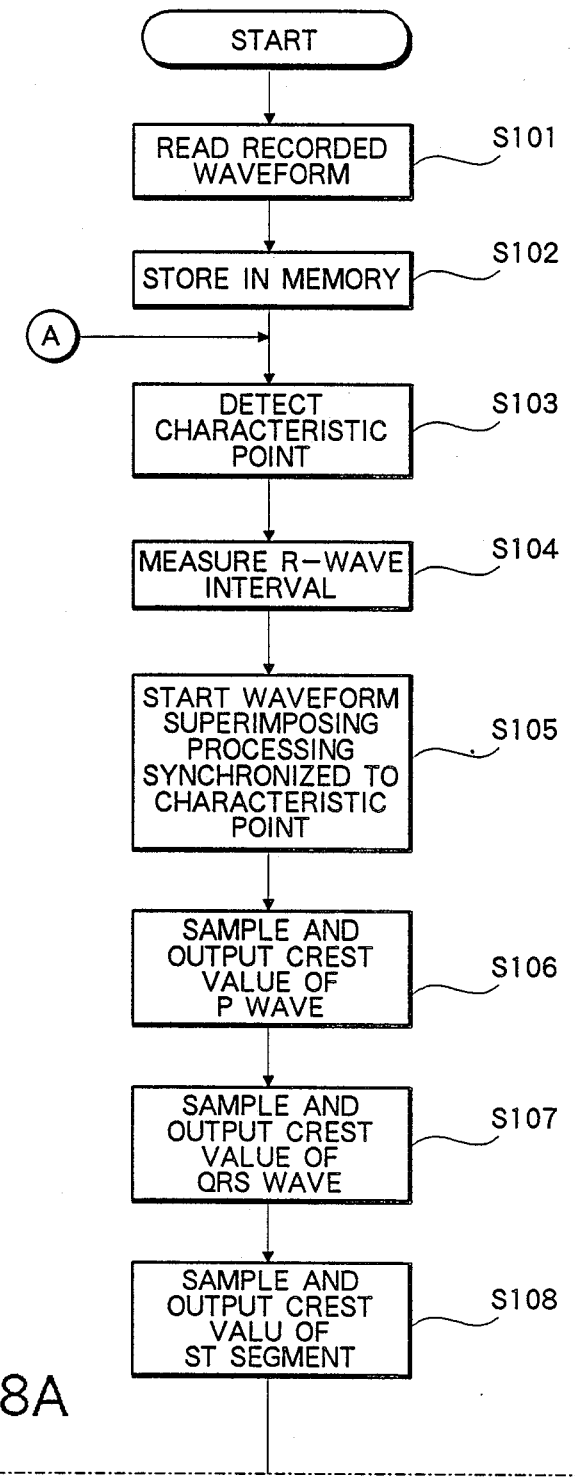
FIGS. 8A and 8B show electrocardiographic waveform output control flowcharts in the third embodiment.
Figure 8B:
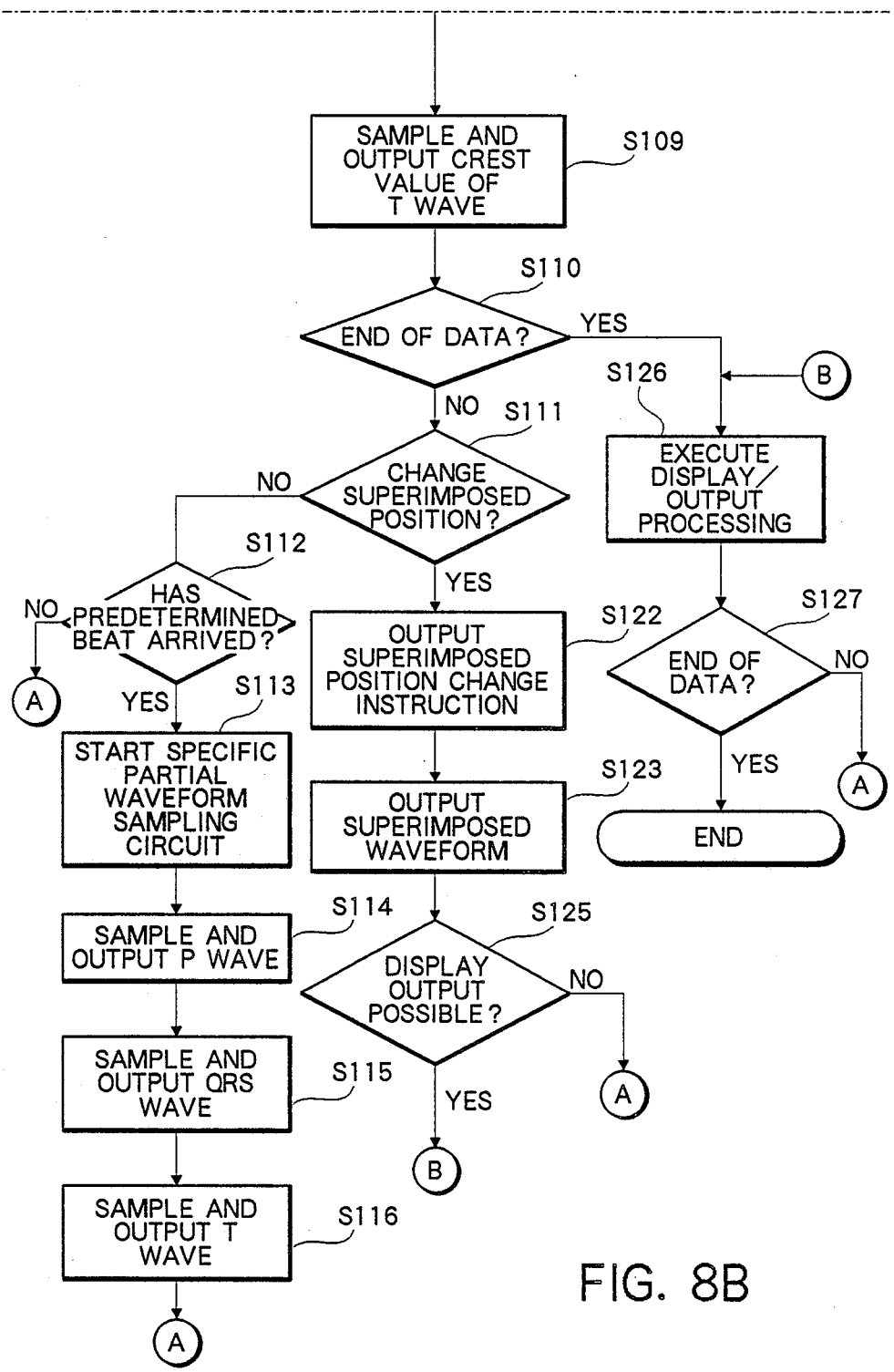

Control of the electrocardiographic output of the apparatus embodied in FIG. 7 will now be described in detail with reference to the flowcharts of FIGS. 8A and 8B.

When the cassette tape 30 having the electrocardiographic waveform recorded by the recording apparatus 20 of FIG. 2 is inserted into the cassette tape reader 13 of the present apparatus and the apparatus is started, the program proceeds to a step S101 in FIG. 8. Here the control unit 11 instructs the reading circuit 14 to control the cassette tape reader 13 so that the recorded electrocardiographic waveform is read out in successive fashion. At this time the read time information is set in the timer circuit 24, which is made to keep track of time at the time of recording. The waveform is written in the memory 15 at a step S102. The capacity of the memory 15 should be sufficient for more than two beats of the electrocardiographic waveform. The steps S101, S102 are subsequently executed continuously and the electrocardiographic waveform read out successively is written in the memory circuit 15. Newly read electrocardiographic waveforms are successively stored upon being superimposed on the oldest electrocardiographic waveforms previously read out. Accordingly, it is necessary for the memory 15 to have the abovementioned storage capacity of at least two beats conforming to processing speed in order that an unprocessed electrocardiographic waveform will not be erased after electrocardiographic waveform processing, described below, ends. Next, at a step S103, the oldest, unprocessed electrocardiographic waveform written in the memory 15 is delivered to the characteristic point detecting circuit 76, where the designated characteristic point, namely the R-wave peak point (e.g., the peak point of the P wave, QRS wave and T wave, the ST measurement point, etc.), is detected. Next, at a step S104, the waveform interval detecting circuit 79 refers to the R-wave peak point detected by the characteristic point detecting circuit 76 and the time measured by the timer circuit 24 to measure the time from the R-wave peak point one beat earlier. The measured time is outputted to the display controller 20 and printer controller 22.

Next, at a step S105, the superimposing circuit 17, in synchronization with the timing of detection of the R-wave peak by the characteristic point detecting circuit 76, superimposes the detected electrocardiographic waveform of the corresponding characteristic point at a timing which is the same as that of the previously superimposed waveform. Accordingly, the R-wave peak points of the superimposed electrocardiographic waveforms all have the same position. At the same time, the characteristic point sampling circuit 78 is started. At a step S106, therefore, the crest value of the P-wave peak (the crest value from the reference level) is found, this is sampled as the P-wave deviation value at this position, and the sampling is outputted to the display controller 20 and printer controller 22. Similarly, the crest value of the QRS-wave peak is found at a step S107, this is sampled as the QRS-wave deviation value at this position, and the sampling is outputted to the display controller 20 and printer controller 22. Next, at a step S108, the ST crest value at a position which prevails upon passage of a predetermined time from the R-wave peak point is found, this is sampled as the ST deviation value at this position, and the sampling is outputted to the display controller 20 and printer controller 22. At a step S109, the T-wave peak crest value is found, this is sampled as the T-wave deviation value at this position, and the sampling is outputted to the display controller 20 and printer controller 22.

The display controller 20 and printer controller 22 which have received these sampled values develop each sampled value on a time axis corresponding to the display output position of page buffers 20a, 22a which store a predetermined amount of the output information containing the sampled values. For example, in the present embodiment, each sampled value is developed so as to be expressed on the same time axis (horizontal axis), thereby enabling the deviation thereof to be recognized with ease.

Also, the R-wave interval is displayed at the same position of the horizontal axis as the others, with the vertical axis serving as the time axis. It is permissible to adopt an arrangement in which the time interval is converted into the heart rate and displayed as the heart rate instead of the R-wave interval.

Next, it is determined at a step S110 whether the recorded information from the cassette tape 30 has stopped arriving. If there is no more recorded information, the program proceeds to a step S126. If there is still recorded information, the program proceeds to a step S111, where it is determined whether a predetermined amount (a predetermined time) of the electrocardiographic waveform has been superimposed. If a predetermined amount (e.g., 128 seconds) has not been superimposed, then the program proceeds to a step S112, where it is determined whether a predetermined amount (or fixed time) of the electrocardiographic waveform has arrived. If the predetermined amount (e.g., 25 beats) has arrived, the program proceeds to a step S113, where the specific partial waveform sampling circuit 75 is started. At a step S114, the circuit 75 samples the P wave of the prevailing electrocardiographic waveform (e.g., the electrocardiographic waveform of the 25th beat) and outputs the sampling to the display controller 20 and printer controller 22. Upon receiving the sampling, the display controller 20 and printer controller 22 develop this partial waveform at a position corresponding to waveform display position in the page buffers. As shown in FIG. 9, the waveform is displayed while changing the display position little by little so as to be displayable within a superimposed electrocardiographic waveform display position, described below. In this embodiment, four or five waveforms are displayed in one superimposed electrocardiographic waveform display position.

Thereafter, in the manner described above, the QRS wave is sampled at a step S115, the T wave is sampled at the step S116, these are outputted to the display controller 20 and printer controller 22. Upon receiving the samplings, the display controller 20 and printer controller 22 develop these partial waveform at positions corresponding to waveform display positions in the page buffers. The program then returns to the step S103 to execute characteristic point detection processing for the next electrocardiographic waveform.

When the predetermined amount (predetermined time) of the electrocardiographic waveform has been superimposed at the step S111, the program proceeds from a step 122, at which a command for altering the superimposed waveform display position is outputted to the superimposing circuit 17, display controller 20 and printer controller 22. The superimposing circuit 17 which has received this command outputs the prevailing superimposed waveform to the display controller 20 and printer controller 22 at a step S123, thereby resetting the superimposed waveform being held. The display controller 20 and printer controller 22 which have received the superimposed waveform develop this superimposed waveform in the page buffers at a position corresponding to the display position. Next, at a step S125, it is determined whether the data developed in the page buffers by the controllers 20, 22 can be outputted, namely whether output data of one outputtable line (or page) has been developed. If it is as yet impossible to output the data, the program returns to the step S103 to execute superimposing processing for the next electrocardiographic waveform.

If it is determined at the step S125 that output of the display is possible, the program proceeds to a step S126, at which the output data developed in the page buffer 20a is displayed on the display unit 21 under the control of the display controller 20 and the output data developed in the page buffer 22a is printed out on the printer 23 under the control of the printer controller 22. In this display/output operation, the superimposed waveform developed in the page buffers 20a, 22a, the trend data and the partial waveform data, etc., are outputted while changing the display position every predetermined time. A detailed example of the outputs is shown in FIG. 9.

In FIG. 9, numeral 151 at the top denotes a change in the R-R wave interval, which is displayed using the vertical axis as a time axis in 'ms' units. Numeral 152 denotes a superimposed graph showing a trend graph, which indicates a change in the crest value of the P-wave peak, and the state of a deviation in the P wave of every predetermined amount of the electrocardiographic waveform. Here the vertical axis indicates the measured potential value in '10 uV' units.

Numeral 153 denotes a superimposed graph in which a trend graph of the crest value of the QRS-wave peak and the QRS wave of every predetermined amount of the electrocardiographic waveform are superimposed, with the vertical axis indicating potential value in '10 uV' units. Numeral 154 denotes the trend graph of any crest value in the ST segment, 155 a graph in which the T-wave peak crest value and the T wave of every predetermined amount of the electrocardiographic waveform are superimposed, and 156 the superimposed waveform of every predetermined amount of the electrocardiographic waveform outputted while changing position. The graphs 151–155 are outputted so as to lie within the same time period in the display position of the superimposed electrocardiographic waveform. In accordance with the abovementioned example, the QRS waves are treated collectively in identical fashion. However, it is possible to adopt an arrangement in which these are treated separately, divided into a Q wave, R wave and S wave and graphed, or in which they are divided into any two waves and outputted.

Thus, each sampling trend graph and partial waveform are outputted, with time corresponding to the interval of the superimposed electrocardiographic waveform display positions serving as the horizontal axis.

When data display and print-out end, the program proceeds to a step S127, at which it is determined whether this is the end of the recorded information. If it is not the end of recorded information, then the program returns to the step S103 to execute processing for the next electrocardiographic waveform. If this is the end of recorded information, on the other hand, then processing is terminated.

In accordance with the embodiment described above, the detected R wave is written in superimposed form in synchronization with the R peak point, and the position at which the R wave is written is shifted at a fixed time interval. This waveform is outputted upon being combined with the R-R interval trend graph and the P-wave crest value trend graph, the P wave and the QRS wave crest value trend graph, the QRS wave, the ST trend graph and the T-wave crest value trend graph, and the T wave, thereby making it possible to easily recognize the extent of change in each electrocardiographic waveform portion and the change in the shape thereof.

Superimposing the waveforms makes it possible to express an entire beat in a small recording area and on a display screen. At such time, the abovementioned partial waveform is developed on the crest value trend position of the peak wave every predetermined waveform (every fixed beat) of the electrocardiographic waveform, whereby the display of the partial waveform where the heartbeat rises becomes more dense so that a change therein can be readily recognized. However, it is permissible to exercise control in such a manner that the electrocardiographic waveform read at a certain time is sampled every predetermined time and the partial waveform displayed. By adopting such control, a change in the waveform every predetermined time can be recognized with ease.

Thus, a predetermined amount of an electrocardiographic waveform is superimposed in synchronization with, e.g., the R wave of the electrocardiographic waveform, and this is displayed while successively changing the display position. Accordingly, the entire waveforms can be displayed in larger size in comparison with the case in which the waveforms are displayed upon being compressed within limits decided by an identical time axis. Consequently, the shape of the electrocardiographic waveform can be easily ascertained even down to very fine portions.

In addition, since a large number of waveforms are superimposed, deviations between waveforms can be recognized very easily. Also, along with the superimposed waveforms, each sampled crest value is displayed while being made to correspond within the same time axis. This makes it possible to easily recognize, even down to very detailed portions, the change with time of more detailed partial waveforms at a glance. A change in a number of electrocardiographic waveforms can thus be recognized very quickly and reliably.

Consequently, when 24 hours of an electrocardiographic waveform is printed out or displayed, the degree of change therein can be ascertained reliably in a short period of time, and observing the change enables an appropriate diagnosis to be made.

In accordance with the invention as described above, a change in an electrocardiographic waveform can be easily recognized and a number of electrocardiographic waveforms can be scrutinized quickly and accurately.

As many apparently widely different embodiments of the present invention can be made without departing from the spirit and scope thereof, it is to be understood that the invention is not limited to the specific embodiments thereof except as defined in the appended claims.

What is claimed is:

1. A method of expressing an electrocardiographic waveform, comprising:
   determining a predetermined characteristic point in a first waveform of said ECG waveform for synchronization of a number of waveforms comprising ECG waveforms to said characteristic point in said first waveform;
   determining a setable predetermined fixed amount of display time during which said ECG waveforms are to be superimposed related in time to said characteristic point; and
   setting a cycle time axis interval which is to occur before the start of said settable fixed amount of time during which said ECG waveforms are to be displayed in superimposition,
   superimposing said number of said superimposed waveforms at expressed positions in visual relationship to an expression of said first waveform and synchronized to said predetermined characteristic point of said first waveform for said predetermined fixed amount of displayed superimposition time to mark a point from which said cycle time axis interval is to be measured;
   said ECG waveforms which are superimposed being selectable from said number of ECG waveforms such that any deviation in the electrocardiographic waveform may be discerned by inspection of the superimposed visual relationship expressed by the displayed superimposition of waveforms.

2. The method according to claim 1, characterized in that the predetermined characteristic point is a QRS segment of the electrocardiographic waveform.

3. The method according to claim 1, characterized in that the predetermined characteristic point is an R wave and expresses an ST deviation in comparative terms.

4. The method according to claim 1, characterized in that an ST trend graph is simultaneously expressed with said superimposed ECG waveforms on a display screen.

5. The method according to claim 1, characterized in that heart rate is simultaneously expressed with said superimposed ECG waveforms on a display screen.

6. The method according to claim 1, characterized in that the level of a desired characteristic point of an ST segment is simultaneously displayed with said superimposed ECG waveforms.

7. An electrocardiographic waveform display apparatus comprising:
   characteristic point detecting means for detecting a predetermined characteristic point contained in an inputted electrocardiographic waveform;
   waveform superimposing means for superimposing a predetermined amount of the electrocardiographic waveform is synchronization with the detected characteristic point;
   output means for displaying and outputting a plurality of electrocardiographic waveforms, which are superimposed by said waveform superimposing means, while changing positions at which the superimposed electrocardiographic waveforms are displayed; and
   setable timing means to set a cycle time axis during which a waveform synchronization signal based upon the detected characteristic point of the waveform is provided to said output means.

8. The apparatus according to claim 7, characterized in that said output means is a printer, said printer having a page buffer for formatting a printed display of a plurality of waveforms which are synchronized and superimposed within a measured time axis.

9. The apparatus according to claim 7, characterized in that said output means is a display device, said display device having a display buffer for displaying successively a plurality of time axis displays of waveforms which are synchronized and superimposed at interval points within the time axis.

10. The apparatus according to claim 7, further comprising trend graph preparing means for preparing a trend graph by sampling values of the electrocardiographic waveform and arbitrary timing positions in synchronization with the characteristic point detected by said characteristic point detecting means, said output means outputting the trend graph along with the superimposed waveforms.

11. The apparatus according to claim 7, further comprising heart rate detecting means for detecting heart rate by measuring an interval at which the electrocardiographic waveform is generated, said output means outputting the heart rate along with the superimposed waveforms.

12. A method of expressing an electrocardiographic waveform, comprising the steps of:
   determining a predetermined characteristic point in a first waveform of said ECG waveform for synchronization of a number of waveforms comprising ECG waveforms to said characteristic point in said first waveform;
   determining a setable predetermined fixed amount of display time during which said ECG waveforms are to be superimposed related in time to said characteristic point; and
   setting a cycle time axis interval which is to occur before the start of said setable fixed amount of time during which said ECG waveforms are to be displayed in superimpositions;
   superimposing said number of said superimposed waveforms at expressed positions in visual relationship to an expression of said first waveform and synchronized to said predetermined characteristic point of said first waveform for said predetermined fixed amount of displayed superimposition time to mark a point from which said cycle time axis interval is to be measured; and wherein,
   said ECG waveforms which are superimposed are selectable from said number of ECG waveforms such that any deviation in the electrocardiographic waveform may be discerned by inspection of the superimposed visual relationship expressed by the displayed superimposition of waveforms; and then,
   displaying a number of superimposed waveforms spaced apart in occurrence over a period of time as a number of superimposed waveforms delimited in time of occurrence from one another by said cycle time axis interval, so as to display in plural form, in a region in which said superimposed ECG waveforms are displayed, at least one specific partial waveform contained in every second predetermined amount of the ECG waveform, and enabling verification of a change in the specific partial waveform of said superimposed waveforms over time.

13. The method according to claim 12, characterized in that a trend graph of a specific point of a predetermined waveform portion in the electrocardiographic waveform is simultaneously displayed in the time axis region in which said superimposed electrocardiographic waveforms are displayed.

14. The method according to claim 13, characterized in that the specific partial waveform includes a P wave, a T wave and a QRS wave and includes a crest value of a P-wave peak, a crest value of a QRS-wave peak, a crest value at any position in an ST segment, and a crest value of a T-wave peak as characteristic points of the predetermined waveform portion, and wherein a trend graph of the crest value of the P-wave peak and the P wave are outputted on the same time axis of the same display region, and a trend graph of the crest value of the QRS-wave peak and the QRS wave are outputted on the same time axis of the same display region and a trend graph of the crest value of the T-wave peak and the T wave are outputted on the same time axis of the same display region.

15. An electrocardiographic waveform display apparatus comprising:
   detecting means for detecting a predetermined characteristic point contained in an inputted electrocardiographic waveform;
   waveform superimposing means for superimposing a predetermined amount of the electrocardiographic waveform in synchronization with the detected characteristic point;
   superimposed waveform output means for displaying and outputting a plurality of electrocardiographic waveforms, which are superimposed by said waveform superimposing means, while positions at which the superimposed waveforms are displayed are changed;
   sampling means for sampling a predetermined partial waveform by a predetermined amount of an inputted electrocardiographic waveform; and
   partial waveform output means for displaying and outputting a plurality of sampled waveforms while changing positions at which the sampled waveforms are displayed.

16. The apparatus according to claim 15, characterized in that said superimposed waveform output means and said partial waveform output means consists of a printer.

17. The apparatus according to claim 15, further comprising trend graph preparing means for preparing a trend graph by sampling values of the predetermined partial waveform, which is sampled by said sampling means, at arbitrary timing positions, said partial waveform output means outputting the trend graph in a form superimposed on an output of the partial waveform.

18. The apparatus according to claim 15, further comprising:
   measuring means for measuring a time interval at which the electrocardiographic waveform is generated; and
   waveform interval output means for outputting results of measurements performed by said measuring means;
   an interval between heartbeats being outputted.

* * * * *